United States Patent [19]

Leon et al.

[11] Patent Number: 5,095,887
[45] Date of Patent: Mar. 17, 1992

[54] MICROSCOPE-ENDOSCOPE ASSEMBLY ESPECIALLY USABLE IN SURGERY

[76] Inventors: Claude Leon; Joseph Leon, both of Hameau de Poggioli, 20144 Sainte Lucie De Porto Vecchio; Jean-Marie Leon, Capo di Lecci, 2017 Porto Vecchio, all of France

[21] Appl. No.: 579,812

[22] Filed: Sep. 10, 1990

[30] Foreign Application Priority Data

Sep. 12, 1989 [FR] France ................. 89 11914

[51] Int. Cl.⁵ .............................................. A61B 1/00
[52] U.S. Cl. ........................................ 128/4; 359/375
[58] Field of Search .................... 128/4, 6; 606/4; 351/205, 216, 218; 350/511, 512, 514

[56] References Cited

U.S. PATENT DOCUMENTS

| | | | |
|---|---|---|---|
| 3,796,220 | 3/1974 | Bredemeier | 128/395 |
| 4,091,814 | 5/1978 | Togo | 606/18 |
| 4,364,629 | 12/1982 | Lang et al. | 350/516 |
| 4,478,499 | 10/1984 | Hoerenz | |
| 4,544,243 | 10/1985 | Munnerlyn | 350/514 |
| 4,580,559 | 4/1986 | L'Esperance | 606/4 |
| 4,657,013 | 4/1987 | Hoerenz et al. | |
| 4,710,000 | 12/1987 | Spitznas et al. | 351/205 |
| 4,723,842 | 2/1988 | Twisselmann et al. | 350/511 |
| 4,744,649 | 5/1988 | Niino et al. | 351/205 |

FOREIGN PATENT DOCUMENTS

| | | |
|---|---|---|
| 3610024 | 9/1986 | Fed. Rep. of Germany |
| 2513772 | 4/1983 | France |
| WO88/04786 | 6/1988 | PCT Int'l Appl. |
| 2140578 | 11/1984 | United Kingdom |

Primary Examiner—Stephen C. Pellegrino
Assistant Examiner—Ralph A. Lewis
Attorney, Agent, or Firm—Curtis, Morris & Safford

[57] ABSTRACT

An optical assembly comprising a microscope (1) including a binocular (3) with a pair of oculars (4, 5), an optical body (8) and an objective lens (9) and an optical path; and an endoscope (2) provided with an extension (10), an outlet ocular (16) and an optical path. A commutating modulus (12, 13, 14; 18, 19, 14) is disposed between the binocular (3) and the optical body (8) of the microscope, and the outlet ocular (16) of the endoscope (2) as to enable an observer whose eyes are located at each ocular (4, 5) of the microscope (1) to observe selectively either: (a) the optical path of the microscope (1), or (b) the optical (or electronic) path of the endoscope (2), or (c) both optical paths simultaneously to scan an object to be investigated.

13 Claims, 4 Drawing Sheets

MICROSCOPE-ENDOSCOPE ASSEMBLY ESPECIALLY USABLE IN SURGERY

BACKGROUND OF THE INVENTION

The present invention relates to a microscope-endoscope assembly which is especially useful in surgery.

Considerable developments have been made during the last years in many fields of surgery. Surgeons have to use increasingly sophisticated devices for either diagnostic or therapeutics purposes.

In certain fields, those skilled in the art use two kinds of devices. i.e. on the one hand a microscope and, on the other hand an endoscope, each having its own unique function. For instance, a typical example wherein these two devices are used is ophthalmic surgery.

Typically, the microscope provides a user with a plan view determined by the intra-ocular members without any possible views of angular areas; i.e. a profile view cannot be provided.

The endoscope allows both angular areas to be viewed and therapeutic means to be introduced.

The use of one device, e.g. the microscope, followed by the use of the other, i.e. the endoscope, does not facilitate accurate determinations or orderly surgical procedures which, of course, are desired. When the microscope and endoscope are used in sequence, the surgeon must alternately look through both oculars of each device. But, this is not easily done and does not enable certain operations to be carried out.

There is a need for a device which enables a surgeon to observe and work while keeping his eyes on the oculars of a single device.

OBJECTS OF THE INVENTION

It is an object of the present invention to satisfy the aforesaid need.

Another object is to provide a compact assembly which enables a surgeon to perform those operations which may be required while keeping his eyes on the oculars of a microscope.

A further object is to facilitate three kinds of observations to be carried out by means of the inventive apparatus:

In a first position, the surgeon or the user uses the optical path of the microscope.

In a second position, the surgeon uses the optical path of the endoscope while looking through the microscope oculars. He does not have to move about and his free hands may be used as necessary. This is important in certain particular fields, such as in ophthalmic surgery where it is known that the endoscope is manipulated in a manner analogous to that of a pencil to orient it in any particular direction needed to obtain a desired good observation.

In a third position, the surgeon looks through the oculars of the microscope along both respective optical paths of the microscope and of the endoscope, and both paths are merged as to provide a single superposed image.

SUMMARY OF THE INVENTION

Accordingly, the present invention relates to an assembly comprising, on the one hand, a microscope having a binocular, an optical body and an objective, and, on the other hand, an endoscope provided with an extension and an outlet ocular, the assembly including a commutating modulus placed between the binocular and the optical body of the microscope and the outlet ocular of the endoscope to enable an observer whose eyes are located at each ocular of the microscope to selectively observe either the optical path of the microscope or the optical or electronic path of the endoscope (if the endoscope is of the electronic type) or simultaneously both the optical path of the microscope and the optical or electronic path of the endoscope to scan the object to be investigated.

As an aspect of the present invention, the commutating modulus is removable and is comprised of at least one optical separator and a reflecting device having their respective normals aligned with the bisectrix between the incident beam and the direction of the respective optical axes;

the distance between the separator and the reflecting device is equal to $1/\sqrt{2}a$ is the axis gap, i.e. the distance between the optical axes of both optical paths of the microscope;

the separator is a glass slab having one face subjected to a semi-reflecting treatment and the reflecting device is a mirror;

the optical means of the endoscope are adapted to that of the microscope by using a dioptric or catadioptric optical system which dimensionally and positionally brings into accord both images formed by the endoscope and the microscope;

the endoscope comprises an outlet ocular providing an image focused for infinity and the microscope provides an image focused for infinity, these images being projected in the space gap between the optical body and the binocular;

the commutating device comprises an internal reflecting prism, a separating cube formed of two prisms and an opaque screen, all being retracted by means of a driving motor;

in one embodiment the dioptric or catadioptric optical system is formed of an air medium;

in another embodiment the dioptric or catadioptric optical system is a mirror;

and in a further embodiment the dioptric or catadioptric optical system is a combination of convergent and divergent lenses of a reflecting prism;

the opaque screen is a metal sheet painted to be light-opaque.

BRIEF DESCRIPTION OF THE DRAWINGS

Various advantages and features of the present invention will appear from the following detailed description with reference to the accompanying drawings in which.

DETAILED DESCRIPTION OF PREFERRED EMBODIMENTS

Figure 1A:
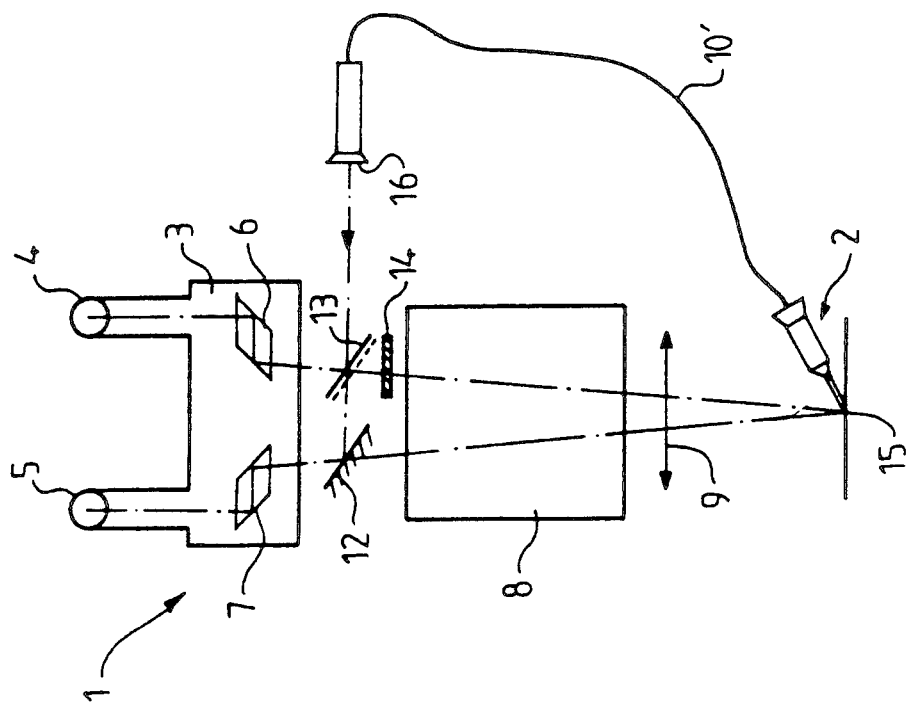
FIGS. 1A and 1B are a general diagrammatic view of the assembly of the invention.

In the accompanying drawings, wherein identical parts are indicated by the same reference symbols and numerals, the microscope is designated by 1 and the endoscope by 2.

As is conventional, the microscope comprises a binocular 3, an optical body 8 and an objective 9. The subject to be investigated is represented by reference numeral 15. The microscope 1 has two oculars 4 and 5 and internal prisms 6 and 7. The endoscope comprises an extension 10 which transmits an outlet image of the endoscope to the inlet of an adapting optical device, i.e. to an outlet ocular 16 of the extension. A supporting ring 11 holds the outlet ocular 16 of extension 10 of endoscope 2 at a desired position.

Figure 1B:
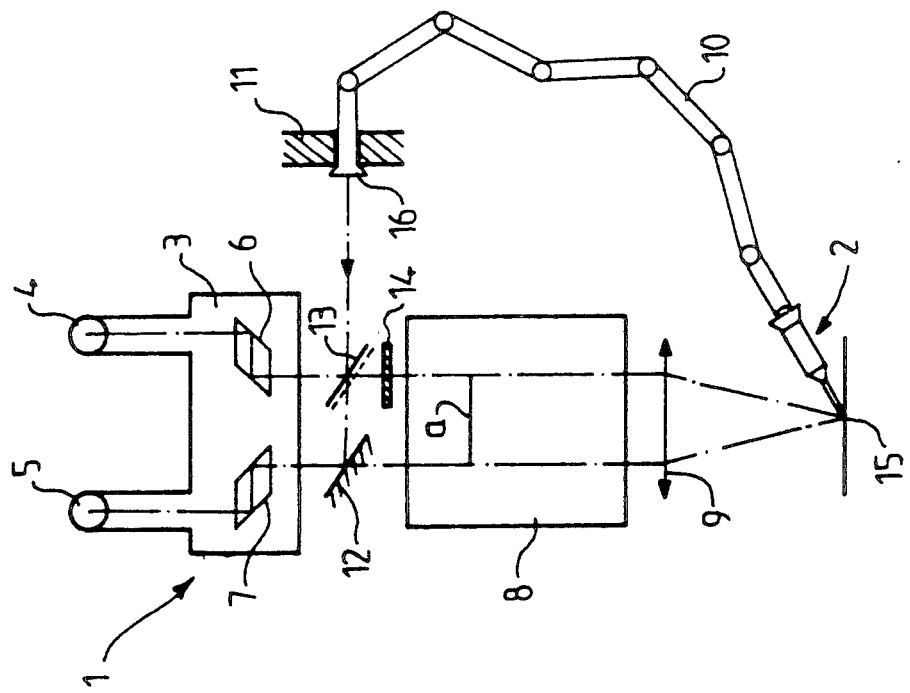

On FIGS. 1A, 1B, a commutating modulus comprises a mirror 12, a separator 13 and an opaque screen 14. The separator 13 is a glass slab having a surface which has been previously subjected to a semi-reflecting treatment as represented by dotted lines. The distance between the separator 13 and the mirror 12 is related to the gap a which is the distance between the optical axes of the two optical paths of the microscope leading to oculars 4 and 5. The distance between the separator 13 and the mirror 12 is preferably equal to $1/\sqrt{2}a$. Generally, the mirror is a plan mirror and the separator is a dioptric slab with parallel sides.

In addition to the distance parameter between the mirror and separator, the orientation thereof comprises a second parameter.

Figure 1C:
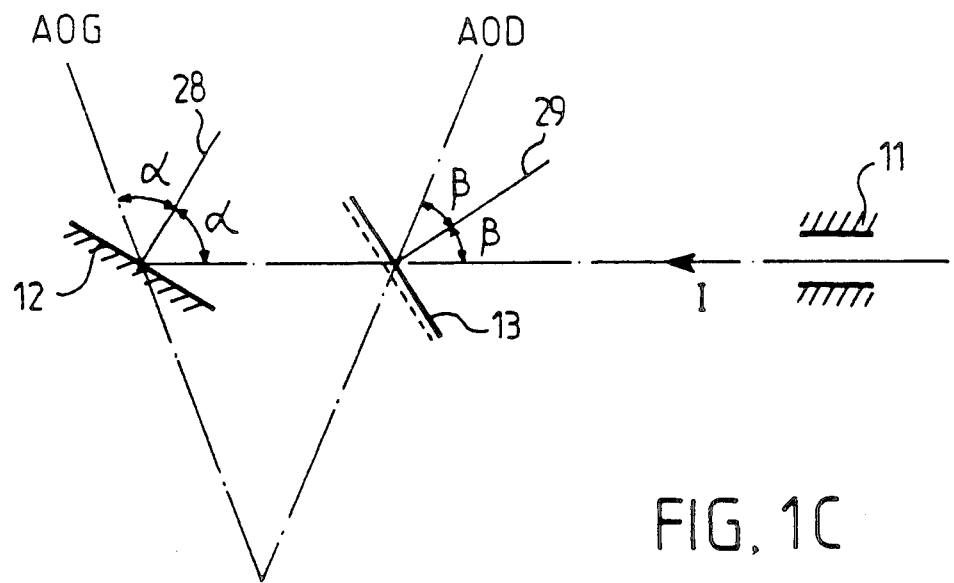
FIG. 1C is a schematic representation of the position relation of the optical members of the commutating modulus.

As illustrated in FIG. 1C, the mirror 12 and the separator 13 are so oriented that each of their respective normals 28 and 29 constitutes the bisectrix of the respective angles $\alpha$ and $\beta$ between the incident optical beam i coming from the endoscope 2 and the direction of the respective optical axes AOG and AOD leading to oculars 4 and 5. The optics of endoscope 2 and of its extension 10 are adapted to the optics of the microscope 1. To this end, use is made of a dioptric or catadioptric optical system which positionally and dimensionally brings into accord the images provided by endoscope 2 and microscope 1.

In the example shown in FIGS. 1A and 1B, this optical system merely consists of an air medium. In this configuration, the air medium is an optical system having a focal magnitude of 1. The endoscope 2 includes an outlet ocular 16 which provides an image focused at infinity whereas the microscope 1 also provides an image focused at infinity within the space gap between optical body 8 and binocular 3. FIG. 1B differs from FIG. 1A in that extension 10 in FIG. 1B includes an optical fiber 10' and does not consist solely of lens and prism assemblies as in FIG. 1A.

The supporting ring 11 may be adjusted as desired by the user under the particular conditions of use.

On FIGS. 1A and 1B, the opaque screen 14 is deliberately located under the separator 13 to mask the right optical path, i.e. that of the separator. With the modulus in the illustrated position, the surgeon may observe subject 15 via the endoscope. Alternatively, when the commutating modulus assembly is retracted, the surgeon can observe subject 15 via the optical path of the microscope. Movement of the modulus to provide this masking effect is preferably provided by any suitable means and may be actuated by means of a pedal to enable the surgeon to use his hands for any other useful operation.

Figure 2:
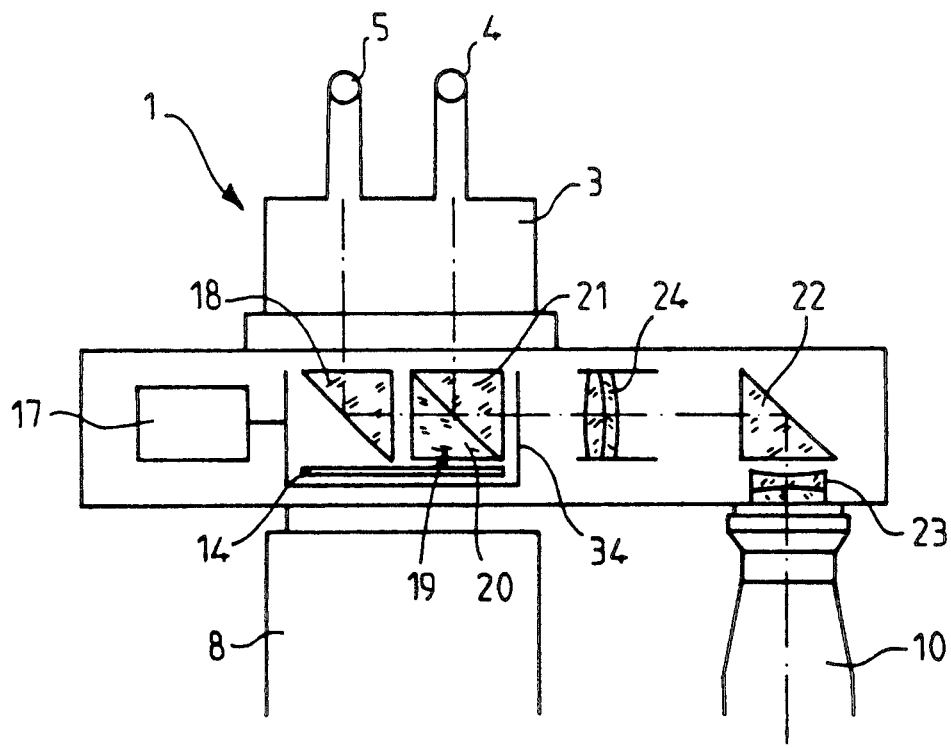
FIG. 2 shows an embodiment comprising a relatively small number of optical members.

FIG. 2 illustrates a practical embodiment of the present invention. Here, the commutating modulus comprises an internal reflecting prism 18, a separating cube 19 formed of two prisms 20 and 21 and the opaque screen 14.

Prisms 18, 20 and 21 are reflecting prisms. Both prisms 20 and 21 are, for example, secured to each other to form the cube, and have undergone a semi-reflecting treatment. This commutating modulus is driven by an electric motor 17 for retracting some or all of the members 18, 19, 14. When the entire assembly is retracted, the user who looks through the oculars 4 and 5 is able to observe the subject by way of the microscope. If desired, the opaque screen 14 may also be retracted separately.

The position of extension 10 of endoscope 2 with respect to microscope 1 shown in FIG. 2 is facilitated by the use of a divergent lens 23, a convergent lens 24 and a reflecting prism 22 mounted between lenses 23, 24. By way of example, the divergent lens 24 is provided with a $-50$ focus, the convergent lens 23 is provided with a 100 focus and the assembly is afocal with a magnitude of 0.5.

In the embodiments shown in the drawings, these positions are provided:

In the first position, the commutating modulus is not retracted and the user looks through both oculars 4 and 5 of microscope 1 along the optical path of the endoscope.

In the second position, the commutating modulus assembly is retracted, and the user looks through both oculars 4 and 5 along the optical path of the microscope.

In the third position, only the opaque screen 14 is retracted, and the user may observe through both the microscope path and the endoscope path which coincide to provide a single image, as in a mixed image.

Figure 3:
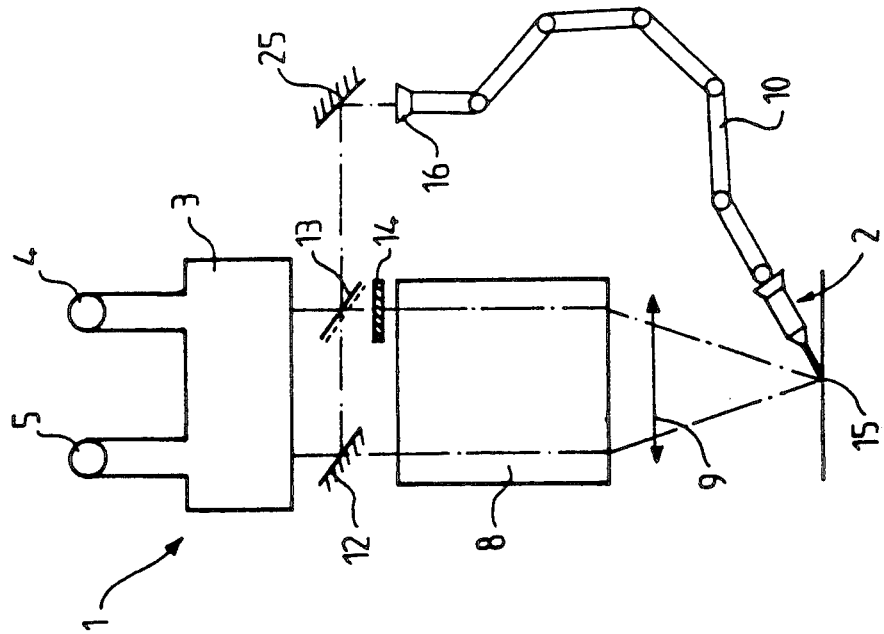
FIG. 3 is an alternative embodiment of the device shown in FIG. 1A.

On FIG. 3, an alternative embodiment is illustrated, wherein use is made of a mirror 25 located in front of the outlet ocular 16 of the extension 10 of endoscope 2. This permits outlet ocular 16 to be disposed in the illustrated configuration.

Figure 4:
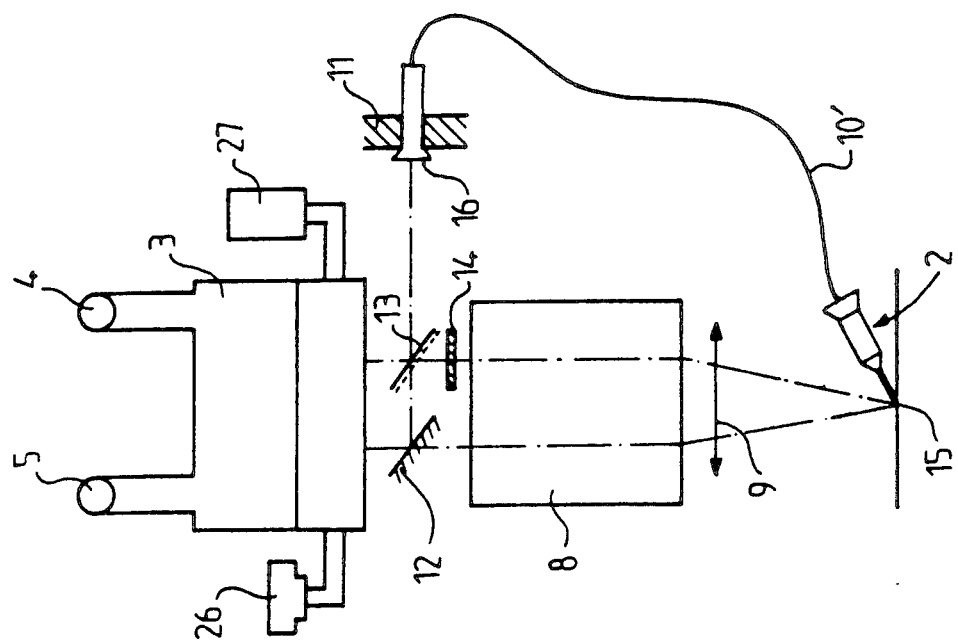
FIG. 4 is another alternative embodiment of the assembly of the invention.

FIG. 4 illustrates the provision of photographic fittings 26 and video apparatus 27 which may be mounted upwards of the optical body 8.

Figure 5:
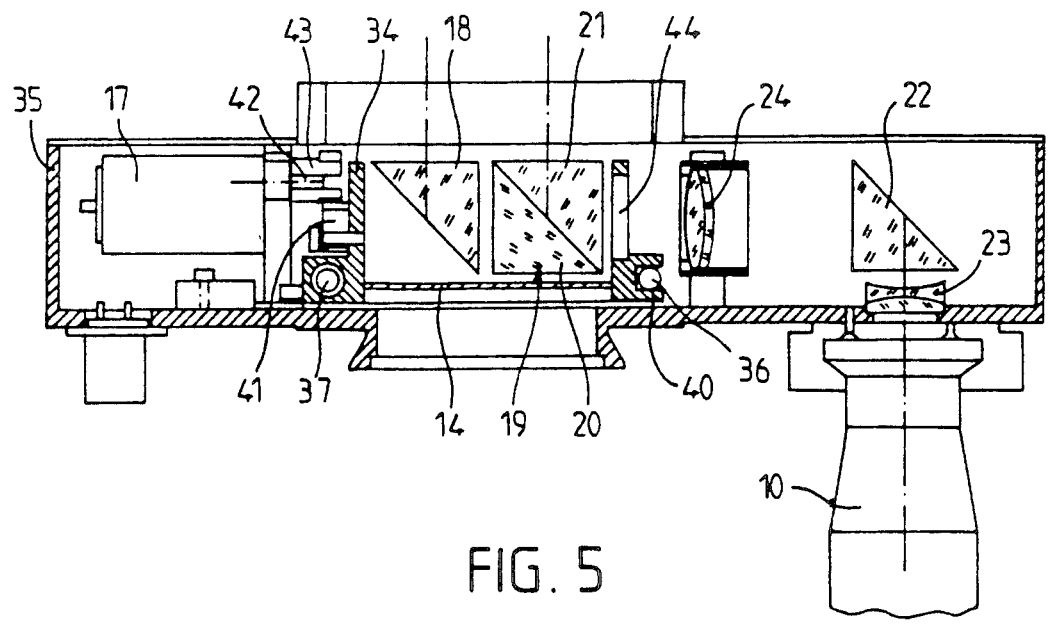
FIG. 5 is a vertical cross-section of an embodiment adapted to retract the commutating modulus.
Figure 6:
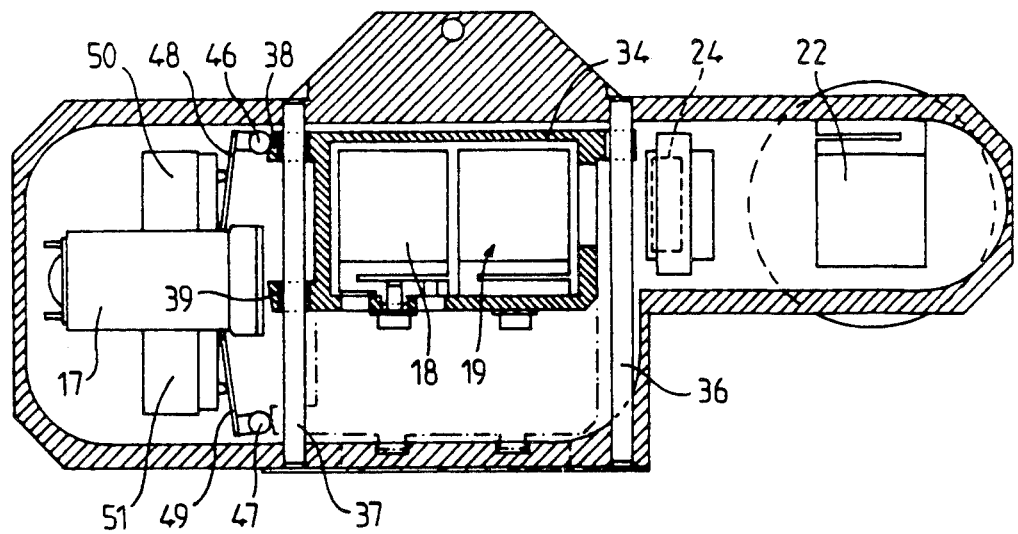
FIG. 6 is a partial plan, partial cross-sectional view of the device shown in FIG. 5.

A displacement operation of the commutating device of the present invention is described with reference to FIGS. 5 and 6, wherein the commutating apparatus includes internal reflecting prism 18 and the separating cube comprising two prisms 20 and 21. The reflecting prism and separating cube are mounted on a carriage 34 which is adapted to slide transversely with respect to a frame 35 on which are secured two parallel columns 36, 37. Guiding on column 37 is ensured by means of coaxial sleeves 38, 39 (FIG. 6) rigidly fixed to the base of carriage 34; and guiding on column 36 is ensured by a bracket 40 (FIG. 5) also rigidly fixed to the base of carriage 34.

A rack mechanism 41 is secured to a side of carriage 34 above sleeves 38, 39 and column 37 and in parallel to the axis of column 37. A reversible electric motor 17 affixed to frame 35 at one side of carriage 34 rotatably drives an output shaft 42 on which is fixed a pinion 43 whose teeth mesh with those of the rack mechanism 41. Thus, when pinion 43 is rotatably driven in either direction by motor 17, the carriage 34 and the optical members supported thereon are moved in a corresponding direction along columns 36 and 37 and between two locations: one being in the optical path of the endoscope and the other being retracted from the optical path of the endoscope. The carriage 34 has a window 44 at the side opposite to the motor 17.

The opaque screen 14 is slidably mounted on gliders provided in the base of the carriage 34 and may be retracted at will when it is desired to look through the optical paths of the microscope.

The electric supply to the motor is switched off when the carriage 34 reaches either of its extreme positions on the frame 35. Either sleeve 38 or sleeve 39 actuates an end-of-travel switch comprising a lug 46 or 47 mounted at the end of a resilient arm 48 or 49 sidely projecting from the motor 17. The deformation or motion of the resilient arm actuates a micro-switch 50 or 51 coupled to the motor to control current supplied thereto.

We claim:

1. An assembly comprising: a microscope including a binocular having a pair of oculars, an optical body, and an objective lens means comprising a first optical path; and endoscope having an extension, and an outlet ocular comprising a second optical; and commutating modulus means disposed between the binocular and the optical body of the microscope and in optical communication with the outlet ocular of the endoscope and selectively operable to enable an observer whose eyes are located at each ocular of the microscope, to observe an image projected along either the first optical path or the second optical path or both optical paths simultaneously.

2. The assembly of claim 1, wherein the commutating modulus means is retractable and is comprised of separator means, reflecting means optically coupled to said separator means along an optic axis aligned with the outlet ocular of said endoscope, and an opaque screen positionable to selectively block the optical path of the microscope, the reflecting means and the separator means having respective normals located on a bisectrix between the axis aligned with the endoscope outlet ocular and respective optical axes to said pair of oculars along the first optical path.

3. The assembly of claim 2 wherein the distance between the separator means and the reflecting means is equal to $1/\sqrt{2}a$ where a is a distance between said respective optical axes.

4. The assembly of claim 2 wherein said opaque screen comprises a metal sheet painted to be light-opaque.

5. The assembly of claim 2 wherein the separator means comprises a glass slab having a semi-reflecting face, and wherein the reflecting means comprises a mirror.

6. The assembly of claim 1 wherein the endoscope and the microscope include similar optical systems for bringing both images formed by the endoscope and the microscope into dimensional and positional alignment.

7. The assembly of claim 1, wherein at least the optical body of said microscope includes an air medium.

8. The assembly of claim 1 wherein the outlet ocular of the endoscope provides an image for infinity and the microscope provides an image for infinity in a gap between the optical body and the binocular.

9. The assembly of claim 1 wherein the commutating modulus means comprises an internal reflecting prism, a separating cube included in said first optical path, optically coupled to said reflecting prism and including two prisms, and an opaque screen selectively blocking said separating cube from said first optical path; and further including a driving motor for retracting said commutating modulus means.

10. The assembly of claim 1 wherein the endoscope includes dioptric optical imaging means.

11. The assembly of claim 1 wherein the endoscope includes catadioptric optical imaging means.

12. The assembly of claim 1, wherein said commutating modulus means comprises a dioptric optical system including convergent and divergent lenses coupled to the endoscope outlet ocular and a reflecting prism optically coupled to said lenses for imaging the second optical path to said commutating modulus means.

13. The assembly of claim 1 wherein said commutating modulus means comprises a catadioptric optical system including convergent and divergent lenses coupled to the endoscope outlet ocular and a reflecting prism optically coupled to said lenses for imaging the second optical path to said commutating modulus means.

* * * * *

UNITED STATES PATENT AND TRADEMARK OFFICE
CERTIFICATE OF CORRECTION

PATENT NO. : 5,095,887
DATED : March 17, 1992
INVENTOR(S) : Claude Leon et al.

It is certified that error appears in the above-identified patent and that said Letters Patent is hereby corrected as shown below:

Claim 1, line 4 (column 5, line 23), before "endoscope" change "and" to --an--;

line 5, (column 5, line 24), after "optical" insert --path--.

Signed and Sealed this

Eleventh Day of May, 1993

Attest:

MICHAEL K. KIRK

Attesting Officer

Acting Commissioner of Patents and Trademarks